United States Patent [19]

Hockley et al.

[11] Patent Number: 4,767,769
[45] Date of Patent: Aug. 30, 1988

[54] ANTIULCER BENZIMIDAZOLE DERIVATIVES

[75] Inventors: Michael H. Hockley, Derbyshire; Roger B. Titman, Nottingham, both of England

[73] Assignee: The Boots Company PLC, England

[21] Appl. No.: 65,363

[22] Filed: Jun. 23, 1987

Related U.S. Application Data

[63] Continuation of Ser. No. 751,616, Jul. 2, 1985, abandoned.

[30] Foreign Application Priority Data

Jul. 5, 1984 [GB] United Kingdom ............... 8417194

[51] Int. Cl.$^4$ ............... A61K 31/445; C07D 401/10
[52] U.S. Cl. ............... 514/322; 514/210; 514/212; 514/253; 514/316; 514/333; 514/338; 514/394; 514/395; 514/228.2; 514/232.5; 514/234.5; 540/524; 540/525; 544/58.1; 544/58.4; 544/58.5; 544/58.6; 544/130; 544/131; 544/139; 544/360; 544/364; 544/370; 546/187; 546/199; 546/256; 546/271; 548/327; 548/329; 548/330
[58] Field of Search ............... 548/330, 327, 329; 540/524, 525; 544/130, 131, 139, 58.1, 58.4, 58.5, 58.6, 364, 360, 370; 546/199, 271, 187, 256; 514/210, 212, 222, 232, 234, 253, 316, 322, 394, 395, 333, 338

[56] References Cited

U.S. PATENT DOCUMENTS

| 2,055,746 | 9/1936 | Hagge ............... 564/305 X |
| 3,147,274 | 9/1964 | Moyle et al. ............... 548/330 |
| 3,182,070 | 5/1965 | Moyle et al. ............... 548/330 |
| 3,256,288 | 6/1966 | Moyle et al. ............... 548/330 |
| 4,362,728 | 12/1982 | Yellin et al. ............... 544/362 X |
| 4,491,586 | 1/1985 | Hayes ............... 546/231 X |
| 4,555,518 | 11/1985 | Rainer ............... 514/338 |
| 4,567,176 | 1/1986 | Brown ............... 514/212 |
| 4,571,394 | 2/1986 | Hayes et al. ............... 514/212 |
| 4,594,425 | 6/1986 | Musser et al. ............... 548/330 X |
| 4,681,883 | 7/1987 | Brown et al. ............... 548/233 X |

FOREIGN PATENT DOCUMENTS

| 0029303 | 10/1980 | European Pat. Off. ............... 548/266 |
| 0050407 | 4/1982 | European Pat. Off. ............... 548/269 |
| 0010063 | 12/1982 | European Pat. Off. ............... 548/327 |
| 0167943 | 1/1986 | European Pat. Off. ............... 548/330 |
| 2157052 | 6/1973 | France ............... 548/330 |
| 2075007 | 11/1981 | United Kingdom ............... 548/266 |
| 1604674 | 12/1981 | United Kingdom ............... 564/47 |
| 2163747 | 3/1986 | United Kingdom ............... 548/330 |

OTHER PUBLICATIONS

Derwent Abstract of EP 10063, 4/16/80.
Derwent Abstracts of JP601 49567, BE 864992 and EP 204215.
Derwent Abstract J60013768.
Chem. Abstracts, 87:151864g (1977).
Chem. Abstracts, 87:151865h (1977).
Chem. Abstracts, 78:136697a (1973).

Primary Examiner—Richard A. Schwartz
Attorney, Agent, or Firm—Jacobs & Jacobs

[57] ABSTRACT

Compounds of formula I

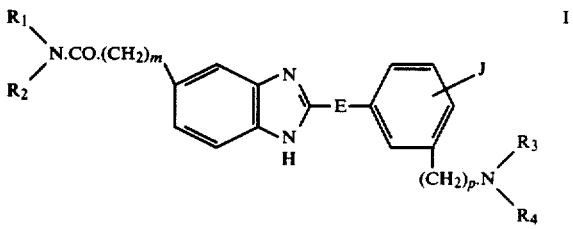

in which $R_1$ and $R_2$, which may be the same or different, are hydrogen, a $C_1$ to $C_3$ alkyl group or $R_1$ and $R_2$ together with the nitrogen to which they are attached form an optionally substituted heterocyclic ring; $R_3$ and $R_4$, which may be the same or different are hydrogen, a $C_1$ to $C_3$ alkyl or an optionally substituted $C_3$ to $C_6$ cycloalkyl group, or $R_3$ and $R_4$ together with the nitrogen to which they are attached form an optionally substituted heterocyclic ring; m is 0, 1 or 2; p is 0, 1 or 2; E is an alkylene group connected to or interrupted by an oxygen or a sulphur atom; J is hydrogen or a substituent group; and their pharmaceutically acceptable salts have utility as histamine $H_2$-receptor antagonists.

32 Claims, No Drawings

ANTIULCER BENZIMIDAZOLE DERIVATIVES

This is a continuation of Ser. No. 751,616, filed July 2, 1985, now abandoned.

The present invention relates to novel compounds having valuable therapeutic properties, to pharmaceutical compositions containing such compounds, to processes for preparing such compounds and to their use in therapy. The compounds have particular utility as histamine $H_2$-receptor antagonists, they inhibit gastric acid secretion and are therefore useful in treating peptic ulcer disease and other conditions caused or exacerbated by gastric acidity.

The present invention provides novel compounds of formula I

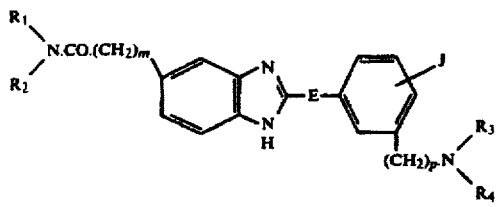

in which $R_1$ and $R_2$, which may be the same or different, are hydrogen, a $C_1$ to $C_3$ alkyl group or $R_1$ and $R_2$ together with the nitrogen to which they are attached form an optionally substituted heterocyclic ring;

$R_3$ and $R_4$, which may be the same or different, are hydrogen, a $C_1$ to $C_3$ alkyl or an optionally substituted $C_3$ to $C_6$ cycloalkyl group, or $R_3$ and $R_4$ together with the nitrogen to which they are attached form an optionally substituted heterocyclic ring;

E is an alkylene group connected to or interrupted by an oxygen or a sulphur atom;

J is hydrogen or a substituent group;

m is 0, 1 or 2; p is 0, 1 or 2;

and their pharmaceutically acceptable acid addition salts.

Preferably the group E contains from 3 to 5 carbon atoms. Suitable groups E are —$(CH_2)_2.S.CH_2$—, —$(CH_2)_3.S$— or —$(CH_2)_n.O$— in which n is 3, 4, or 5. Preferred groups E are —$(CH_2)_n.O$— in which n is 3 or 4.

When J is a substituent group, preferably the group is an electron withdrawing group such as a halo or nitro group. More preferably the group J is hydrogen, chloro or nitro.

In a preferred compound provided by the invention E represents $(CH_2)_n.O$, in which n is 3 or 4, and J represents hydrogen.

When $R_1$ and/or $R_2$ are alkyl groups the groups may be methyl, ethyl, propyl or isopropyl. When $R_1$ and $R_2$ together with the nitrogen to which they are attached form a heterocyclic ring that ring may contain a total of 4, 5, 6 or 7 atoms. The ring may contain a further heteroatom (for example a nitrogen atom, a sulphur atom or an oxygen atom) in addition to the nitrogen atom to which $R_1$ and $R_2$ are attached and may contain a double bond. When the heterocyclic ring is substituted the substituents may be $C_1$ to $C_3$ alkyl groups (for example methyl groups) which may be attached to a carbon atom or any further nitrogen atom present in the ring. Examples of suitable heterocyclic rings are pyrrolidinyl, piperidino, hexamethyleneimino, tetrahydropyridyl, piperazinyl, morpholino, thiomorpholino, methylpyrrolidinyl, methylpiperzinyl, methylpiperidino or azetidinyl. Advantageously the group $NR_1R_2$ is amino, methylamino, dimethylamino, isopropylamino, ethylmethylamino, diethylamino, pyrrolidinyl, piperidino, morpholino, methylpyrrolidinyl, methylpiperazinyl or azetidinyl. Preferbly the group $NR_1R_2$ is amino, methylamino, dimethylamino, piperidino or pyrrolidinyl.

When $R_3$ and/or $R_4$ are alkyl groups the groups may be methyl, ethyl, propyl or isopropyl. When $R_3$ and/or $R_4$ are cycloalkyl groups the groups may be cyclopropyl, cyclobutyl, cyclopentyl, cyclohexyl optionally substituted by alkyl groups containing 1 to 3 carbon atoms, for example methyl groups. When $R_3$ and $R_4$ together with the nitrogen to which they are attached form a heterocyclic ring that ring may contain a total of 4, 5, 6 or 7 atoms. The ring may contain a further heteroatom (for example a nitrogen atom, a sulphur atom or an oxygen atom) in addition to the nitrogen atom to which $R_3$ and $R_4$ are attached and may contain a double bond. When the heterocyclic ring is substituted the substituents may be $C_1$ to $C_3$ alkyl groups (for example methyl groups) which may be attached to a carbon atom or any further nitrogen atom present in the ring or hydroxy groups. Examples of suitable heterocyclic rings are pyrrolidinyl, piperidino, hexamethyleneimino, tetrahydropyridyl, piperazinyl, morpholino, thiomorpholino, methylpyrrolidinyl, methylpiperazinyl, methylpiperidino or hydroxypiperidino. Advantageously the group $NR_3R_4$ is methylamino, dimethylamino, diethylamino, ethylmethylamino, propylamino, pyrrolidinyl, piperidino, hexamethyleneimino, tetrahydropyridyl, morpholino, methylpyrrolidinyl, methylpiperidino, hydroxypiperidino, cyclohexylamino or cyclopropylamino. Preferably the group $NR_3R_4$ is dimethylamino, propylamino, piperidino or pyrrolidinyl.

Preferred compounds of formula I are those in which m and p are 1 and E represents $(CH_2)_n.O$ in which n is 3 or 4.

Compounds of formula I may exist as solvates or as salts with pharmaceutically acceptable acids. Examples of such salts include hydrochlorides, hydrobromides, sulphates, methanesulphonates, maleates, acetates, citrates, fumarates, tartrates, di-p-toluoyltartrates, succinates, lactates and salts with dicarboxylic amino acids such as aspartic and glutamic acids. Such salts may exist in the form of solvates (for example hydrates).

Specific compounds of formula I provided by the invention are:

5-Methylcarbamoylmethyl-2-[3-(3-piperidinomethylphenoxy)propyl]benzimidazole

5-Methylcarbamoylmethyl-2-[3-(3-pyrrolidin-1-ylmethylphenoxy)propyl]benzimidazole 5-Pyrrolidin-1-ylcarbonylmethyl-2-[3-(3-pyrrolidin-1-ylmethylphenoxy)propyl]benzimidazole 2-[3-(3-Piperidinomethylphenoxy)propyl]-5-pyrrolidin-1-ylcarbonylmethylbenzimidazole 2-[3-(3-Dimethylaminomethylphenoxy)propyl]-5-pyrrolidin-1-ylcarbonylmethylbenzimidazole 2-[3-(3-Hexamethyleneiminomethylphenoxy)propyl]-5-pyrrolidin-1-ylcarbonylmethylbenzimidazole 2-[3-(3-Cyclohexylaminomethylphenoxy)propyl]-5-pyrrolidin-1-ylcarbonylmethylbenzimidazole 2-{3-[3-(4-Methylpiperidinomethyl)phenoxy]propyl}-5-pyrrolidin-1-ylcarbonylmethylbenzimidazole 2-[3-(3-Morpholinomethylphenoxy)propyl]-5-pyrrolidin-1-ylcarbonylmethylbenzimidazole 2-{3-[3-(2-Methylpyrrolidin-1-ylmethyl)phenoxy]-
propyl}-5-pyrrolidin-1-ylcarbonylmethylbenzimidazole
2-[3-(3-Dimethylaminophenoxy)propyl]-5-pyrrolidin-1-ylcarbonylmethylbenzimidazole
2-[3-(3-Methylaminomethylphenoxy)propyl]-5-pyrrolidin-1-ylcarbonylmethylbenzimidazole
5-Pyrrolidin-1-ylcarbonylmethyl-2-{3-[3-(2-pyrrolidin-1-ylethyl)phenoxy]propyl}benzimidazole
2-[3-(3-Propylaminomethylphenoxy)propyl]-5-pyrrolidin-1-ylcarbonylmethylbenzimidazole
2-{3-[3-(1,2,3,6-Tetrahydro-1-pyridylmethyl)phenoxy]propyl}-5-pyrrolidin-1-ylcarbonylmethylbenzimidazole
5-Piperidinocarbonylmethyl-2-[3-(3-pyrrolidin-1-ylmethylphenoxy)propyl]benzimidazole
5-(2-Dimethylcarbamoylethyl)-2-[3-(3-piperidinomethylphenoxy)propyl]benzimidazole
2-[3-(3-Piperidinomethylphenoxy)propyl]-5-(2-pyrrolidin-1-ylcarbonylethyl)benzimidazole
5-Dimethylcarbamoylmethyl-2-[3-(3-piperidinomethylphenoxy)propyl]benzimidazole
5-(2-Methylpyrrolidin-1-ylcarbonylmethyl)-2-[3-(3-pyrrolidin-B 1-ylmethylphenoxy)propyl]benzimidazole
2-[3-(3-Dimethylaminomethylphenoxy)propyl]-5-(4-methylpiperazin-1-ylcarbonylmethyl)benzimidazole
2-[3-(3-Diethylaminomethylphenoxy)propyl]-5-dimethylcarbamoylmethylbenzimidazole
2-[3-(3-Dimethylaminomethylphenoxy)propyl]-5-isopropylcarbamoylmethylbenzimidazole
2-[3-(3-Dimethylaminomethylphenoxy)propyl]-5-N-ethyl-N-methylcarbamoylmethylbenzimidazole
2-[3-(3-Dimethylaminomethylphenoxy)propyl]-5-dimethylcarbamoylmethylbenzimidazole
2-[3-(3-Dimethylaminomethylphenoxy)propyl]-5-morpholinocarbonylmethylbenzimidazole
5-Dimethylcarbamoylmethyl-2-[3-(3-N-ethyl-N-methylaminomethylphenoxy)propyl]benzimidazole
5-Diethylcarbamoylmethyl-2-[3-(3-dimethylaminomethylphenoxy)propyl]benzimidazole
2-[4-(3-Piperidinomethylphenoxy)butyl]-5-pyrrolidin-1-ylcarbonylmethylbenzimidazole
5-Dimethylcarbamoyl-2-[3-(3-piperidinomethylphenoxy)propyl]benzimidazole
5-Carbamoylmethyl-2-[3-(3-piperidinomethylphenoxy)propyl]benzimidazole
2-[3-(4-Chloro-3-piperidinomethylphenoxy)propyl]-5-methylcarbamoylmethylbenzimidazole
2-{3-[3-(4-Hydroxypiperidinomethyl)phenoxy]propyl}-5-methylcarbamoylmethylbenzimidazole
2-{3-[3-(3-Hydroxypiperidinomethyl)phenoxy]propyl}-5-methylcarbamoylmethylbenzimidazole
2-[3-(3-Cyclopropylaminomethylphenoxy)propyl]-5-methylcarbamoylmethylbenzimidazole
5-Methylcarbamoylmethyl-2-[5-(3-piperidinomethylphenoxy)pentyl]benzimidazole
5-Azetidin-1-ylcarbonylmethyl-2-[3-(3-piperidinomethylphenoxy)propyl]benzimidazole
2-[3-(3-Dimethylaminomethylphenoxy)propyl]-5-methylcarbamoylmethylbenzimidazole
5-Methylcarbamoylmethyl-2-[2-(3-piperidinomethylbenzylthio)ethyl]benzimidazole
5-Methylcarbamoylmethyl-2-[3-(3-piperidinomethylphenylthio)propyl]benzimidazole
5-Methylcarbamoylmethyl-2-[3-(4-nitro-3-piperidinomethylphenoxy)propyl]benzimidazole
2-[3-(2-Chloro-3-piperidinomethylphenoxy)propyl]-5-methylcarbamoylmethylbenzimidazole and their pharmaceutically acceptable acid addition salts.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The active ingredient inside the capsule may be formulated in sustained release form. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat peptic ulceration and other conditions caused or exacerbated by gastric acidity in human beings. In such treatment the amount of the compound of formula I administered per day is in the range 1 to 1500 mg preferably 25 to 800 mg.

The processes described hereinafter for the preparation of compounds of formula I form a further aspect of the present invention.

Compounds of formula I may be be prepared by the reaction of a diamine of formula II

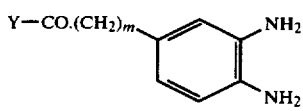
II in which Y is a group of formula $-NR_1R_2$ and $R_1$, $R_2$ and m are as defined with respect to formula I with a compound of formula III

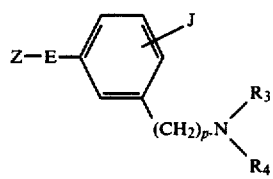
III in which J, E, $R_3$, $R_4$ and p are as defined with respect to formula I and Z is (a) an imidate group of formula IV

IV or a salt thereof in which A is an oxygen atom and in which $R_5$ is an alkyl group preferably an alkyl group containing 1 to 4 carbon atoms which is optionally substituted e.g. $R_5$ may be benzyl, (b) a cyano group, (c) a carboxylic acid group of formula $-COOH$, (d) a carboxylic acid halide group, for example a group of formula $-COCl$, (e) a carboxylic ester group for example a group of formula $-COOR_6$ in which $R_6$ is an optionally substituted alkyl group preferably containing 1 to 4 carbon atoms, (f) a carboxylic amide group such as a group of formula $-CONH_2$, (g) a formyl group, (h) an acetal group of formula $-CH(OR_7)_2$ in which $R_7$ is an optionally substituted alkyl group preferably containing 1 to 4 carbon atoms (for example Z may be a dimethoxymethyl group of formula $-CH(OMe)_2$), (i) an amidine group or a substituted amidine group (such as an N-phenylamidine group) or salts thereof, (j) an imidoyl halide group preferably a group of formula $-C(Cl)=NR_8$ in which $R_8$ is an optionally substituted alkyl group preferably containing 1 to 4 carbon atoms or an aryl group preferably a phenyl group, (k) a thioimidate group of formula IV or a salt thereof in which A is a sulphur atom and $R_5$ is as defined above or (l) an orthoester group for example a group of formula $C(OR_{10})_3$ where $R_{10}$ is an optionally substituted alkyl group, preferably containing 1 to 4 carbon atoms. In the preparation of compounds of formula I in which $R_3$ and/or $R_4$ are H by the above method, the group $-NR_3R_4$ may be protected for example by the formation of a phthalimide when $R_3$ and $R_4$ are both H.

Compounds of formula I may be prepared from compounds of formula V

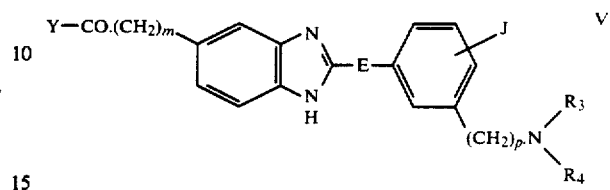
V in which Y is a hydroxy group or an alkoxy group of formula $-OR_9$ in which $R_9$ is an optionally substituted alkyl group preferably containing 1 to 4 carbon atoms and E, J, $R_3$, $R_4$, m and p are as defined with respect to formula I, by the conversion of the group $-COY$ into the group $-CONR_1R_2$ by methods which are well known to those skilled in the art for preparing amides from acids or esters.

Compounds of formula I may be prepared by the reaction of compounds of formula VI

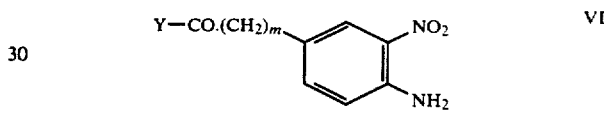
VI in which Y is a group of formula $-NR_1R_2$ in which $R_1$, $R_2$ and m are as defined with respect to formula I with compounds of formula III in which Z is any one of the groups described above (except for a formyl group, an acetal group or an orthoester group) to give compounds of formula VII

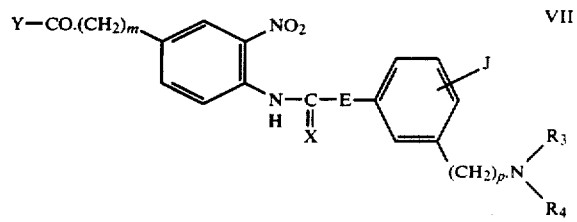
VII in which X has the meaning given below in Table A, Y is a group of formula $-NR_1R_2$ and E, J, $R_1$, $R_2$, $R_3$, $R_4$, m and p are as defined with respect to formula I, followed by reductive cyclisation of the compounds of formula VII to give compounds of formula I

TABLE A

| Z in Formula III | X in Formula VII |
|---|---|
| imidates or salts thereof | NH |
| cyano | NH |
| $-COOH$ | O |
| $-COCl$ | O |
| $-COOR_6$ | O |
| $-CONH_2$ | O |
| amidines or salts thereof | NH |
| $\underline{N}$—phenyl amidine or salts thereof | NPh |
| $-C(Cl)=NR_8$ | $NR_8$ |

Compounds of formula I may be prepared by the reaction of compounds of formula VI in which Y is a group of formula $NR_1R_2$ with a compound of formula III to which Z is a formyl group or an acetal group to give compounds of formula VIII

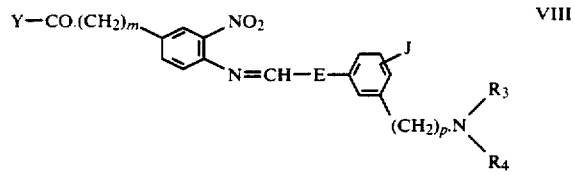

in which Y is a group of formula $NR_1R_2$ and E, J, $R_1$, $R_2$, $R_3$, $R_4$, m and p are as defined with respect to formula I followed by reduction of the nitro group and oxidative cyclisation to give compounds of formula I.

Compounds of formula I may be prepared by the cyclisation of compounds of formula IX

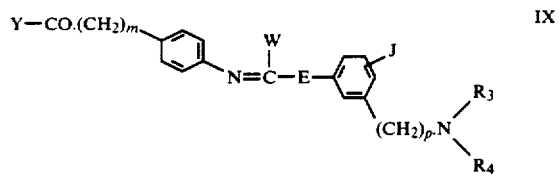

in which Y is a group of formula $-NR_1R_2$ and W is a group of formula $-NH_2$ and E, J, $R_1$, $R_2$, $R_3$, $R_4$, m and p are as defined with respect to formula I for example by reaction with lead tetraacetate.

Preferred compounds provided by the invention, in which J is hydrogen and E is $-(CH_2)_n.O$ in which n is 3 or 4, may be prepared by any of the above-mentioned processes for the preparation of compounds of formula I.

Diamine compounds of formula II in which Y is a group of formula $-NR_1R_2$ or $-OR_9$ may be prepared by the reduction, for example with sodium dithionite or reduced iron, of the corresponding 2-nitroanilines of formula VI. 2-Nitroanilines of formula VI in which Y is a group of formula $-NR_1R_2$ may be prepared by the reaction of 2-nitroanilines of formula VI in which Y is a group of formula $-OR_9$ with an amine of formula $R_1R_2NH$. 2-Nitroanilines of formula VI in which Y is a group of formula $-OR_9$ may be prepared (a) by the nitration of an ester of 4-aminobenzoic acid (m=0) or an ω-(4-aminophenyl)alkanoic acid (m=1 or 2) in which the amino group has been protected, for example by acylation, followed by deprotection of the amino group or (b) by alcoholysis of a cyano compound of formula X

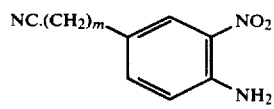

in which m is 0, 1 or 2, which is prepared by the nitration of 4-aminobenzonitrile (m=0) or an ω-(4-aminophenyl)alkanonitrile (m=1 or 2) in which the amino group is protected, for example by acylation, and deprotection of the amino group.

Compounds of formula III in which Z is an imidate group may be prepared by the basification of compounds of formula III in which Z is an imidate salt group which may be prepared by the reaction of an acid and an alcohol of formula $R_5OH$ (for example ethanol in the presence of hydrogen chloride which may be mixed with dioxan to give an imidate salt in which $R_5$ is ethyl) on compounds of formula III in which Z is a cyano group. Compounds of formula III in which Z is a group of formula $-COOH$ may be prepared by hydrolysis of compounds of formula III in which Z is a group of formula $-COOR_6$ or in which Z is a cyano group. Compounds of formula III in which Z is a group of formula $-COCl$, $-COOR_6$ or $-CONH_2$ may be prepared from compounds of formula III in which Z is a group of formula $-COOH$ by methods well known in the art. Compounds of formula III in which Z is a group of formula $-COOR_6$ may be prepared by the alcoholysis of compounds of formula III in which Z is a cyano group. Compounds of formula III in which Z is a group of formula $CONH_2$ may be prepared by mild hydrolysis of compounds of formula III in which Z is a cyano group as is well known in the art. Compounds of formula III in which Z is a formyl group may be prepared by the reduction of compounds of formula III in which Z is a cyano group, for example, with diisobutylaluminium hydride. Compounds of formula III in which Z is an acetal group of formula $-CH(OR_7)_2$ may be prepared by the reaction of an alcohol of formula $R_7OH$ with compounds of formula III in which Z is a formyl group in the presence of an acid catalyst. Compounds of formula III in which Z is an amidine group may be prepared (a) by the action of ammonia on compounds of formula III in which Z is a salt of an imidate group or (b) by the action of ammonium chloride on compounds of formula III in which Z is an imidate group. Compounds of formula III in which Z is an N-phenylamidine salt may be prepared by the reaction of ammonia with compounds of formula III in which Z is an imidoyl chloride of formula $-C(Cl)=NPh$. Compounds of formula III in which Z is an imidoyl chloride of formula $-C(Cl)=NR_8$ may be prepared by the reaction of thionyl chloride on the corresponding amides (i.e. compounds of formula III in which Z is a group of formula $-CONHR_8$). Compounds of formula III in which Z is a thioimidate group or a salt thereof may be prepared by the alkylation, for example with an alkyl halide, of thioamides prepared, for example, by the reaction of phosphorus pentasulphide on compounds of formula III in which Z is a group of formula $-CONH_2$. Compounds of formula III in which Z is a group of formula $-C(OR_{10})_3$ may be prepared by the reaction of an alcohol of formula $R_{10}OH$ on compounds of formula III in which Z is a salt of an imidate group.

Compounds of formula III in which Z is one of a cyano group, a formyl group or a group of formula $-COOH$, $-COOR_6$, $-CONH_2$, $-CH(OR_7)_2$ or $-C(OR_{10})_3$ and E is a group of formula $(CH_2)_nO$ may be prepared by the reaction of phenols of formula XI

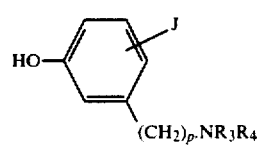

in which J, $R_3$, $R_4$, n and p are as defined with respect to formula I with a compound of formula $Z(CH_2)_nX'$ in which X' is a leaving group for example a bromo group. Alternatively compounds of formula III in which Z is a cyano group and E is a group of formula (CH$_2$)$_n$O may be prepared by the reaction of phenols of formula XI with a compound of formula X"(CH$_2$)$_n$X' in which X" is a leaving group for example a chloro group followed by the replacement of the group X" by a cyano group.

Compounds of formula III in which E is a group of formula (CH$_2$)$_n$O, p is 1 or 2, Z is one of a cyano group, a formyl group or a group of formula —COOH, —COOR$_6$, —CONH$_2$, —CH(OR$_7$)$_2$ or —C(OR$_{10}$)$_3$ and R$_3$ and R$_4$ are H may be prepared by the following series of reactions: (i) the reaction of a 3-methoxybenzyl halide or a 3-methoxyphenethyl halide (for example 3-methoxybenzyl chloride) with potassium phthalimide (ii) the reaction of the resulting product, for example, with pyridine hydrochloride to convert the methoxy group into a hydroxy group, (iii) reaction of the resulting phenol with a compound of formula Z.(CH$_2$)$_n$X' and (iv) reaction of the product with, for example, aqueous methylamine.

Compounds of formula III in which E is a group of formula (CH$_2$)$_n$O, p=1 and Z is one of a cyano group, a formyl group or a group of formula —COOH, —COOR$_6$, —CONH$_2$, —CH(OR$_7$)$_2$ or —C(OR$_{10}$)$_3$ may be prepared by the reaction of a compound of formula Z(CH$_2$)$_n$X' with 3-hydroxybenzaldehyde followed by conversion of the aldehyde group into a group of formula —CH$_2$NR$_3$R$_4$ for example by reductive amination.

Compounds of formula III in which E is a group of formula (CH$_2$)$_3$S may be prepared by methods analogous to those described hereinbefore for the preparation of compounds of formula III in which E is a group of formula (CH$_2$)$_n$O except that the phenol is replaced by the corresponding thiophenol. Compounds of formula III in which E is a group of formula (CH$_2$)SCH$_2$ may be prepared by the reaction of a compound of formula Z(CH$_2$)$_2$X' with a benzylisothiourea which may be prepared by the reaction of thiourea and the corresponding benzyl halide for example the corresponding benzyl chloride.

Compounds of formula V in which Y is a group of formula —OR$_9$ may be prepared (a) by the reaction of diamines of formula II in which Y is an alkoxy group of formula —OR$_9$ with compounds of formula III in which Z is any of the groups described above except for an imidate group or a salt thereof or a thioimidate group or a salt thereof (b) by the reaction of compounds of formula VI in which Y is a group of formula —OR$_9$ with compounds of formula III in which Z is any one of the groups described above (except for a formyl group, an acetal group or an orthoester group) to give compounds of formula VII in which X has the meaning given in Table A above followed by reductive cyclisation of the compound of formula VII (c) by the reaction of compounds of formula VI in which Y is a group of formula —OR$_9$ with a compound of formula III in which Z is a formyl or an acetal group to give compounds of formula VIII followed by reduction of the nitro group and oxidative cyclisation (d) by the cyclisation of compounds of formula IX in which Y is a group of formula —OR$_9$ and W is a group of formula —NH$_2$ for example by reaction with lead tetraacetate. Compounds of formula V in which Y is a hydroxy group may be prepared by reactions similar to those described immediately above for the preparation of compounds of formula V in which Y is a group of formula —OR$_9$. Compounds of formula V in which Y is a hydroxy group may be prepared by the cyclisation of compounds of formula IX in which Y is a hydroxy group or a group of formula —OR$_9$ and W is a group of formula NH$_2$ by reaction with sodium hypochlorite followed by sodium carbonate. Compounds of formula V in which Y is a hydroxy group and m=0 may be prepared by the hydrolysis of the product of the reaction between 4-cyano-o-phenylenediamine and a compound of formula III in which Z is any one of the groups listed above except for an imidate group or a salt thereof or a thioimidate group or a salt thereof. Compounds of formula V in which Y is a group of formula —OR$_9$ and m=0 may be prepared by alcoholysis of the product of the reaction between 4-cyano-o-phenylenediamine and a compound of formula III in which Z is any one of the groups listed above except for an imidate group or a salt thereof or a thioimidate group or a salt thereof. Compounds of formula V in which Y is a hydroxy group may be converted by known methods into esters of formula V in which Y is a group of formula —OR$_9$. Compounds of formula V in which m=1 may be prepared (a) by the homologation of compounds of formula V in which m=0 by methods which are well known in the art for example via the alcohol produced by reduction of compounds of formula V in which m=0 and Y is a hydroxy group or a group of formula OR$_9$ or (b) by the conversion of the acetyl compound prepared by the reaction of 4-acetyl-o-phenylenediamine with a compound of formula III in which Z is any one of the groups listed above except for an imidate group or a salt thereof or a thioimidate group or a salt thereof, for example, by the reaction of thallium trinitrate in methanol to give compounds of formula V in which Y=OMe. Compounds of formula V in which m=1 and Y is a hydroxy group may be prepared by the conversion, for example by the Willgerodt-Kindler reaction of the acetyl compound prepared by the reaction of 4-acetyl-o-phenylenediamine with a compound of formula III in which Z is any one of the groups listed above except for an imidate group or a salt thereof or a thioimidate group or a salt thereof.

Compounds of formula IX in which E, J, R$_1$, R$_2$, R$_3$, R$_4$, R$_9$ m and p are as hereinbefore defined and W is a group of formula NH$_2$ may be prepared by reaction of compounds of formula XII

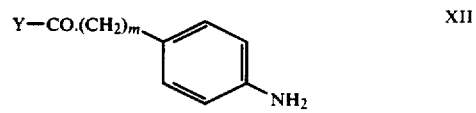

in which Y is a hydroxy group, a group of formula —OR$_9$ or a group of formula NR$_1$R$_2$ with compounds of formula III in which Z is an imidate group or a salt thereof or a thioimidate group or a salt thereof or by reaction of compounds of formula XII in which Y is OR$_9$ or NR$_1$R$_2$, in which R$_1$ and R$_2$ are not both hydrogen, with a compound of formula III in which Z is a cyano group, in the presence of a Lewis acid, for example aluminium chloride. Compounds of formula IX in which W is a group of formula —NH$_2$ and Y is a group of formula OR$_9$ or a group of formula —NR$_1$R$_2$ in which R$_1$ and R$_2$ are not both H may be prepared for example by the reaction of ammonia on compounds of formula IX in which W is a chlorine atom which may be prepared for example by the reaction of thionyl chloride with the amide formed by the reaction of compounds of formula III in which Z is a group of formula —COCl with an amine of formula XII.

Phenols of formula XI in which p=1 may be prepared by the reductive amination of m-hydroxybenzaldehyde by reacting the benzaldehyde with an amine of formula $HNR_3R_4$ in the presence of formic acid or a reducing agent such as sodium borohydride or sodium cyanoborohydride. Phenols of formula XI in which one or both of $R_3$ and $R_4$ are other than H may be prepared by the alkylation of compounds of formula XIII

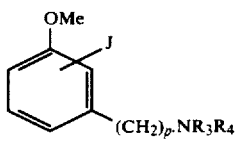

XIII in which J, $R_3$, $R_4$ and p are as defined with respect to formula I, in which one or both of $R_3$ and $R_4$ are H followed by conversion of the methoxy group into a hydroxy group for example by reaction with hydrogen bromide. Compounds of formula XIII in which $R_3$ and $R_4$ are H may be prepared by the reduction, for example with borane dimethyl sulphide complex of 3-methoxybenzonitrile to give compounds of formula XIII in which p=1 or of 3-methoxyphenylacetonitrile to give compounds of formula XIII in which p=2.

The invention further provides intermediate compounds of formula II

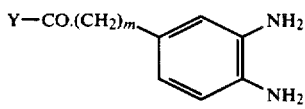

II in which Y is $NR_1R_2$ in which $R_1$ and $R_2$, which may be the same or different, are hydrogen, a $C_1$ to $C_3$ alkyl group or $R_1$ and $R_2$ together with the nitrogen to which they are attached form an optionally substituted heterocyclic ring; and m=0, 1 or 2; with the proviso that when m is 0, Y is not $NH_2$.

Specific intermediate compounds of formula II provided by the invention are:
4-Pyrrolidin-1-ylcarbonylmethyl-o-phenylenediamine;
4-Piperidinocarbonylmethyl-o-phenylenediamine;
4-(4-Methylpiperazin-1-ylcarbonylmethyl)-o-phenylenediamine;
4-(2-Methylpyrrolidin-1-ylcarbonylmethyl)-o-phenylenediamine;
4-Morpholinocarbonylmethyl-o-phenylenediamine;
4-(2-Pyrrolidin-1-ylcarbonylethyl)-o-phenylenediamine;
4-Azetidin-1-ylcarbonylmethyl-o-phenylenediamine;
4-Methylcarbamoylmethyl-o-phenylenediamine;
4-Dimethylcarbamoylmethyl-o-phenylenediamine;
4-N-Ethyl-N-methylcarbamoylmethyl-o-phenylenediamine;
4-Diethylcarbamoylmethyl-o-phenylenediamine;
4-Isopropylcarbamoylmethyl-o-phenylenediamine;
4-(2-Dimethylcarbamoylethyl)-o-phenylenediamine;
4-Carbamoylmethyl-o-phenylenediamine.

The invention also provides intermediate compounds of formula III

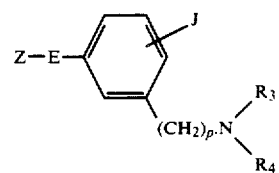

III in which E is an alkylene group connected to or interrupted by an oxygen or a sulphur atom;

J is hydrogen or a substituent group;

$R_3$ and $R_4$, which may be the same or different, are hydrogen, a $C_1$ to $C_3$ alkyl or an optionally substituted $C_3$ to $C_6$ cycloalkyl group, or $R_3$ and $R_4$ together with the nitrogen to which they are attached form an optionally substituted heterocyclic ring;

p is 0, 1 or 2; and

Z is an imidate group of formula IV

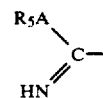

IV or a salt thereof, in which A is an oxygen atom and $R_5$ is an optionally substituted alkyl group; with the proviso that when E is $(CH_2)_n.O$ in which n is 3 or 4, J=hydrogen and p is 1, $NR_3R_4$ is not piperidino.

Specific intermediate compounds of formula III provided by the invention are:
Ethyl 4-(3-piperidinomethylphenoxy)butyrimidate;
Ethyl 4-(3-pyrrolidin-1-ylmethylphenoxy)butyrimidate;
Ethyl 4-(3-hexamethyleneiminomethylphenoxy)butyrimidate;
Ethyl 4-[3-(4-methylpiperidinomethyl)phenoxy]butyrimidate;
Ethyl 4-[3-(1,2,3,6-tetrahydro-1-pyridylmethyl)phenoxy]butyrimidate;
Ethyl 4-(3-morpholinomethylphenoxy)butyrimidate;
Ethyl 4-[3-(2-methylpyrrolidin-1-ylmethyl)phenoxy]butyrimidate;
Ethyl 4-(3-methylaminomethylphenoxy)butyrimidate;
Ethyl 4-(3-dimethylaminomethylphenoxy)butyrimidate;
Ethyl 4-(3-diethylaminomethylphenoxy)butyrimidate;
Ethyl 4-(3-N-ethyl-N-methylaminomethylphenoxy)butyrimidate;
Ethyl 4-(3-propylaminomethylphenoxy)butyrimidate;
Ethyl 4-(3-cyclohexylaminomethylphenoxy)butyrimidate;
Ethyl 4-[3-(4-hydroxypiperidinomethyl)phenoxy]butyrimidate;
Ethyl 4-(3-cyclopropylaminomethylphenoxy)butyrimidate;
Ethyl 4-[3-(3-hydroxypiperidinomethyl)phenoxy]butyrimidate;
Ethyl 5-(3-piperidinomethylphenoxy)valerimidate;
Ethyl 6-(3-piperidinomethylphenoxy)hexanoimdate;
Ethyl 4-(4-chloro-3-piperidinomethylphenoxy)butyrimidate;
Ethyl 4-(2-chloro-3-piperidinomethylphenoxy)butyrimidate;
Ethyl 4-(4-nitro-3-piperidinomethylphenoxy)butyrimdate;
Ethyl 4-[3-(2-pyrrolidin-1-ylethyl)phenoxy]butyrimidate;

Ethyl 4-(3-dimethylaminophenoxy)butyrimidate;
Ethyl 3-(3-piperidinomethylbenzylthio)propionimidate;
Ethyl 4-(3-piperidinomethylphenylthio)butyrimidate,
and acid addition salts thereof, for example hydrochlorides.

The invention also provides intermediate compounds of formula VI

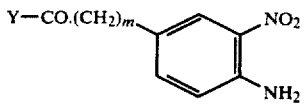

in which Y is a group of formula $-NR_1R_2$ in which $R_1$ and $R_2$, which may be the same or different, are hydrogen, a $C_1$ to $C_3$ alkyl group or $R_1$ and $R_2$ together with the nitrogen to which they are attached form an optionally substituted heterocyclic ring; and m is 0, 1 or 2.

Specific intermediate compounds of formula VI provided by the invention are:
2-Nitro-4-pyrrolidin-1-ylcarbonylmethylaniline;
2-Nitro-4-piperidinocarbonylmethylaniline;
4-(4-Methylpiperazin-1-ylcarbonylmethyl)-2-nitroaniline;
4-(2-Methylpyrrolidin-1-ylcarbonylmethyl)-2-nitroaniline;
4-Morpholinocarbonylmethyl-2-nitroaniline;
2-Nitro-4-(2-pyrrolidin-1-ylcarbonylethyl)aniline;
4-Azetidin-1-ylcarbonylmethyl-2-nitroaniline;
4-Methylcarbamoylmethyl-2-nitroaniline;
4-Dimethylcarbamoylmethyl-2-nitroaniline;
4-N-Ethyl-N-methylcarbamoylmethyl-2-nitroaniline;
4-Diethylcarbamoylmethyl-2-nitroaniline;
4-Isopropylcarbamoylmethyl-2-nitroaniline;
4-(2-Dimethylcarbamoylethyl)-2-nitroaniline;
4-Carbamoylmethyl-2-nitroaniline.

The invention will be illustrated by the following Examples in which Examples 1 to 16 describe the preparation of diamines of formula II, Examples 17 to 42 describe the preparation of compounds of formula III and Examples 43 to 95 describe the preparation of compounds of formula I. The product of each Example was characterised by conventional laboratory techniques such as elemental analysis, infrared spectroscopy, proton magnetic resonance spectroscopy, mass spectroscopy and chromatography.

EXAMPLE 1

A solution of ethyl 4-amino-3-nitrophenylacetate (30 g) and pyrrolidine (150 ml) in ethanol (750 ml) was heated under reflux for 72 hours. Further portions of pyrrolidine (75 and 30 ml) were added after 24 and 48 hours respectively. On cooling 2-nitro-4-pyrrolidin-1-ylcarbonylmethylaniline (m.p. 157°–159° C.) was deposited as orange plates.

A mixture of sodium dithionite (245 g) and sodium carbonate (196 g) in water (1129 ml) and methanol (1029 ml) was stirred and 2-nitro-4-pyrrolidin-1-ylcarbonylmethylaniline (30.5 g) was added over a period of five minutes. A further portion of water (1468 ml) was added and the solution was heated under reflux for 65 minutes. The volume was reduced in vacuo in several stages with any solid material removed by filtration between each stage. Any solid so removed was washed with methanol and the washings combined with the final filtrate. The resulting solution was evaporated to dryness and the residue dried by azeotropic distillation with toluene and then ethanol. The dried residue was extracted with boiling ethanol and the solution filtered to give a solution which yielded 4-pyrrolidin-1-ylcarbonylmethyl-o-phenylenediamine (m.p. 105°–108° C.) on evaporation.

In a similar manner to that described in Example 1 the nitroanilines of formula VI and diamines of formula II listed in Table I were prepared. In each case the course of the reaction was followed using thin layer chromatography and where the desired reaction was incomplete, heating was continued and additional reactants were added as necessary.

TABLE I

| Example | Y | m | m.p. (°C.) of nitroanilines of formula VI | m.p. (°C.) of diamines of formula II | Notes |
|---|---|---|---|---|---|
| 2 | piperidino | 1 | 126–129 | 97–102 | |
| 3 | 4-methyl-piperazin-1-yl | 1 | 147–150 | | (1)(2) |
| 4 | 2-methyl pyrrolidin-1-yl | 1 | 93–97 | | (1)(2) |
| 5 | morpholino | 1 | 163 | 125 | |
| 6 | pyrrolidin-1-yl | 2 | 137–138 | 133–134 | |
| 7 | azetidin-1-yl | 1 | 138–141 | | (3) |

(1) No solvent other than the amine was used in the preparation of the nitroaniline.
(2) Diamines isolated as gums which were used without further purification.
(3) Diamine isolated as an oil which was used without further purification.

EXAMPLE 8

A mixture of ethyl 4-amino-3-nitrophenylacetate (22.4 g) and a 33% (w/v) solution (124 ml) of methylamine in ethanol was stirred at room temperature for 24 hours during which time 4-methylcarbamoylmethyl-2-nitroaniline (m.p. 165°–169° C.) separated from solution.

The resulting nitroaniline (16.45 g) was added to a stirred suspension of sodium dithionite (157 g) and sodium carbonate (239 g) in water (1664 ml) and methanol (668 ml) and the solution heated under reflux for two hours. The volume was reduced to ca. 500 ml by evaporation. Any solid precipitating was removed by filtration and washed with methanol. The washings were added to the filtrate and the mixture evaporated to dryness. The residue was dried by azeotropic distillation with toluene and then ethanol. The resulting brown solid was extracted with boiling ethanol. The extract was filtered whilst hot and 4-methylcarbamoylmethyl-o-phenylenediamine (m.p. 136°–138° C.) precipitated from the filtrate on cooling.

EXAMPLE 9

A solution of ethyl 4-amino-3-nitrophenylacetate (25 g) in a 33% (w/v) solution (500 ml) of methylamine in ethanol was heated in an autoclave for 6½ hours at 150° C. at a pressure of 20–25 atmospheres. After cooling, the volume of the mixture was reduced by evaporation until crystallisation of 4-methylcarbamoylmethyl-2-nitroaniline (m.p. 165°–169° C.) occurred.

The nitroaniline prepared above was then reduced to give 4-methylcarbamoylmethyl-o-phenylenediamine (m.p. 136°–138° C.) in a similar manner to that described in Example 8.

In a similar manner to that described in Example 9 the nitroanilines of formula VI and diamines of formula II listed in Table II were prepared. The following Notes relate to Table II.

Notes (1) Diamine was an oil boiling point of which was not determined.

(2) The reaction mixture obtained after autoclaving was evaporated to dryness and the residue dissolved in ethyl acetate. The extract was washed with water and the solvent removed to leave a residue which was treated as described in Note (3) or (4) below.

(3) The nitroaniline was crystallised from isopropanol.

(4) The nitroaniline was purified by flash chromatography.

(5) The diamine was isolated as a mixture with inorganic contaminants. The structure of the organic component was confirmed spectroscopically.

(16) The reaction mixture obtained after autoclaving was evaporated to dryness and the residue digested with hot ethanol. Concentration and cooling of the solution gave a brown solid which was discarded. The solution was evaporated to dryness and the residue triturated whilst hot with ethanol to give the nitroaniline as an orange solid.

TABLE II

| Ex. | Y | m | A | B | C | D | E | Notes |
|---|---|---|---|---|---|---|---|---|
| 10 | dimethylamino | 1 | 15–20 | 100–120 | 13 | 167–168 | — | (1) |
| 11 | ethylmethylamino | 1 | 30 | 150 | 60 | 90–94 | — | (1)(2)(3) |
| 12 | diethylamino | 1 | 20 | 150 | 43 | 115 | — | (1)(2)(4) |
| 13 | isopropylamino | 1 | 20 | 150 | 48 | 183–187 | — | (3)(5) |
| 14 | dimethylamino | 2 | 20–25 | 150 | 28 | 125–128 | 140–144 | (5) |
| 15 | amino | 1 | 20 | 150 | 132 | 189–193 | 108–110 | (6) |

A = autoclave pressure (atmospheres)
B = autoclave temperature (°C.)
C = time in autoclave (hours)
D = m.p. of nitroaniline VI (°C.)
E = m.p. of diamine II (°C.)

EXAMPLE 16

Reduced iron powder (9.87 g) and then a solution of ammonium chloride (0.373 g) in water (37 ml) were added to a solution of 4-methylcarbamoylmethyl-2-nitroaniline prepared as described in Example 8 (3.34 g) in industrial methylated spirit (186 ml). The mixture was heated under reflux for one hour and was then filtered through diatomaceous earth (sold under the trade name CELITE). The solid material collected was washed with hot industrial methylated spirit. The solvent was removed by evaporation an the residue dried by azeotropic distillation with toluene. The dried residue was recrystallised from industrial methylated spirit to give 4-methylcarbamoylmethyl-o-phenylenediamine (m.p. 140°–142° C.).

EXAMPLE 17

Sodium borohydride (1.52 g) was added to a stirred solution of 3-hydroxybenzaldehyde (4.9 g) and piperidine (6.8 g) in ethanol (25 ml) cooled in an ice-water bath. The mixture was stirred at ambient temperature for 16 hours and then poured into water (250 ml) and the resulting mixture acidified with 2N hydrochloric acid. The acidified mixture was extracted with ethyl acetate and the aqueous phase was made alkaline by the addition of aqueous ammonia solution (S.G. 0.880) to yield N-3-hydroxybenzylpiperidine (m.p. 135°–139° C.) as a colourless solid.

A mixture of N-3-hydroxybenzylpiperidine (9.55 g) and anhydrous potassium carbonate (13.8 g) in dimethylformamide (100 ml) was stirred at ambient temperature for 17 hours. 4-Bromobutyronitrile (5 ml) was added and the mixture stirred at ambient temperature for 24 hours. Water (10 volumes) was added and the resulting mixture extracted with ethyl acetate. The extracts were washed with water, dried and the solvent removed to leave an oil which was purified by distillation (190°–200° C./0.1 mm) or by chromatography on a column packed with an activated magnesium silicate (sold under the trade name FLORISIL) to give 4-(3-piperidinomethylphenoxy)butyronitrile as an oil.

In a similar manner the compounds of formula III in which Z is cyano, J is hydrogen, E is —$(CH_2)_3$.O and p=1 listed in Table III were prepared as oils and were characterised by chromatographic and spectroscopic methods.

TABLE III

| Example | $NR_3R_4$ | Purification method |
|---|---|---|
| 18 | pyrrolidin-1-yl | distillation 180° C./0.15 mm Hg |
| 19 | hexamethyleneimino | chromatography |
| 20 | 4-methylpiperidino | chromatography |
| 21 | 1,2,5,6-tetrahydropyrid-1-yl | chromatography |
| 22 | morpholino | distillation 164–167° C./0.025 mm Hg |
| 23 | 2-methylpyrrolidin-1-yl | chromatography |
| 24 | methylamino | chromatography |
| 25 | dimethylamino | chromatography |
| 26 | diethylamino | no purification of oil undertaken |
| 27 | ethylmethylamino | no purification of oil undertaken |
| 28 | propylamino | chromatography |
| 29 | cyclohexylamino | chromatography |
| 30 | 4-hydroxypiperidino | chromatography |
| 31 | cyclopropylamino | chromatography |
| 32 | 3-hydroxypiperidino | no purification of oil undertaken |

EXAMPLE 33

In a similar manner to that described in Example 17, 5-(3-piperidinomethylphenoxy)valeronitrile (b.p. 160°–164° C./0.1 mm Hg) was prepared by the reaction of N-3-hydroxybenzylpiperidine with 5-bromovaleronitrile.

EXAMPLE 34

N-(3-Hydroxybenzyl)piperidine (9.55 g) was heated with 6-bromohexanenitrile (10.2 g) and potassium carbonate (13.8 g) under reflux in acetone (150 ml) for 66 hours. The reaction mixture was cooled and filtered. The solvent was removed by evaporation and the residue was heated with stirring at 100° C. for one hour to remove unreacted 6-bromohexanenitrile and to yield 6-(3-piperidinomethylphenoxy)hexanenitrile as an oil.

EXAMPLE 35

In a similar manner to that described in Example 17 4-(4-nitro-3-piperidinomethylphenoxy)butyronitrile was prepared by the reaction of 5-hydroxy-2-nitrobenzaldehyde (10 g) with piperidine (12.3 ml) and sodium borohydride (2.7 g) in absolute ethanol (68 ml) to give N-(5-hydroxy-2-nitrobenzyl)piperidine which was then reacted with 4-bromobutyronitrile (4.1 ml) to give the above-mentioned product.

EXAMPLE 36

In a similar manner to that described in Example 17 4-(4-chloro-3-piperidinomethylphenoxy)butyronitrile was prepared by the reaction of 2-chloro-5-hydroxybenzaldehyde (1.379 g), piperidine (1.8 ml) and sodium borohydride (0.33 g) in absolute ethanol (10 ml) to produce N-(2-chloro-5-hydroxybenzyl)piperidine which was then reacted with 4-bromobutyronitrile to yield the above-mentioned product.

EXAMPLE 37

In a similar manner to that described in Example 17 2-chloro-3-hydroxybenzaldehyde (9 g) in absolute ethanol (60 ml) was treated with piperidine (11.7 ml) and sodium borohydride (2.2 g) to yield N-(2-chloro-3-hydroxybenzyl)piperidine. The piperidine thus prepared was reacted with 4-bromobutyronitrile to give 4-(2-chloro-3-piperidinomethylphenoxy)butyronitrile.

EXAMPLE 38

Thionyl chloride (650 ml) was added dropwise to a stirred suspension of 3-methoxyphenylacetic acid (500 g) in chloroform (650 ml) over ca 10 mins. The cloudy solution was heated to reflux for 4½ hours and then allowed to cool to room temperature. The excess thionyl chloride and chloroform were removed by distillation. The cooled residue was dissolved in dry ether (1 liter) and poured onto iced aqueous ammonia solution (S.G. 0.880, 3.5 l). 3-Methoxyphenylacetamide (m.p. 124°-127° C.) was deposited.

Thionyl chloride (1249 ml) was added dropwise to dry dimethylformamide (400 ml) stirring at 0°-5° C. under nitrogen over a period of about 2 hours. 3-Methoxyphenylacetamide (403.7 g) was added portionwise over a period of 45 minutes to the above solution under nitrogen maintaining the temperature between 0°-5° C. The reaction mixture was then stirred at 0°-5° C. for a further 2 hours. The reaction mixture was poured carefully onto ice/water (6 l). The aqueous mixture was extracted with ether. The extracts were washed with water, dried over magnesium sulphate and evaporated in vacuo to give a red liquid. The crude product was distilled (110°-112° C./12 mm Hg) to give 3-methoxyphenylacetonitrile.

Borane dimethyl sulphide (45 ml) was added dropwise to a stirred solution of 3-methoxyphenylacetonitrile (32.4 g) in dry tetrahydrofuran (150 ml) under nitrogen. The solution was heated under reflux for 2 hours and was then cooled to 0° C. The solution was stirred under nitrogen at 0° C. as water (74 ml) was added, followed by concentrated hydrochloric acid (149 ml) dropwise over 1 hour. The cloudy solution was heated on a steam bath for 4 hours and then allowed to cool to room temperature. The suspension was diluted with 5N hydrochloric acid (30 ml) and the acidic mixture was washed with ether then basified with 5N sodium hydroxide and extracted with ether. The extracts were washed with water, dried and evaporated to yield a residue which was dissolved in dry ether (50 ml). A saturated solution of hydrogen chloride in ethanol (30 ml) was added followed by more dry ether (150 ml) and the mixture was cooled to 0° C. to yield 2-(3-methoxyphenyl)ethylamine hydrochloride (m.p. 121°-123° C.). The hydrochloride (27.3 g) was dissolved in 5N sodium hydroxide (100 ml) and extracted with ether. The extracts were washed with water (50 ml) and dried. The solvent was removed by evaporation to give the free base.

A stirred suspension of anhydrous sodium carbonate (0.923 g), 2-(3-methoxyphenyl)ethylamine (0.5 g) and 1,4-dibromobutane (0.43 ml) in dry xylene (5.5 ml) was heated under reflux for 16 hours. The reaction mixture was allowed to cool to room temperature and was filtered. The filtrate was extracted with 5N hydrochloric acid. The acidic extracts were washed with ether and then basified with 5N sodium hydroxide solution and extracted with ether. The ether extracts were washed with water, dried and the ether removed by evaporation to give 3-(2-pyrrolidin-1-ylethyl)anisole.

A solution of the anisole (9.99 g) in 48% hydrobromic acid (400 ml) was heated under reflux for 7 hours and was then allowed to cool to room temperature. The reaction mixture was further cooled to 0° C. and excess aqueous ammonia solution (S.G. 0.880) was added with stirring. The basic mixture was extracted with ether. The extract was washed with water, dried and the solvent was removed by evaporation to yield 3-(2-pyrrolidin-1-ylethyl)phenol (m.p. 99°-102.5° C.).

A suspension of the phenol (0.66 g) and anhydrous potassium carbonate (0.95 g) in dry dimethylformamide (8 ml) was stirred at room temperature for 16 hours. 4-Bromobutyronitrile (0.51 g) was added and the suspension was stirred at room temperature for 24 hours. The reaction mixture was poured into water (80 ml) and extracted with ethyl acetate. The extract was washed with water, dried and the solvent removed by evaporation to yield a residue which was heated under vacuum to remove excess 4-bromobutyronitrile. The resultant material was dissolved in 3% acetone/petroleum ether (b.p. 60°-80° C.) and purified by chromatography on a column packed with an activated magnesium silicate (sold under the trade name FLORISIL) to yield 4-[3-(2-pyrrolidin-1-ylethyl)phenoxy]butyronitrile.

EXAMPLE 39

A suspension of 3-dimethylaminophenol (5 g), potassium carbonate (10.05 g) and dimethylformamide (85 ml) was stirred at room temperature for 5 hours. 4-Bromobutyronitrile (7.3 ml) was added and the suspension stirred for 17 hours. The reaction mixture was poured into water and extracted with ethyl acetate. The extracts were washed with water, dried and the solvent removed to yield 4-(3-dimethylaminophenoxy)butyronitrile.

EXAMPLE 40

Lithium aluminium hydride (5 g) was added portionwise to a stirred solution of methyl 3-piperidinocarbonylbenzoate (12.9 g) in dry tetrahydrofuran (200 ml) under nitrogen and the mixture was stirred under reflux for 3 hours. Excess reducing agent was destroyed by the dropwise addition of water under nitrogen with cooling. The reaction mixture was filtered through diatomaceous earth (sold under the trade name CELITE) which was washed with water and ethyl acetate and then the organic layer was separated. The aqueous layer was washed with ethyl acetate. The combined extracts were washed with water, dried and evaporated to give 3-piperidinomethylbenzylalcohol.

A solution of the above alcohol (2.05 g) in dry dichloromethane (60 ml) was treated with a solution of thionyl chloride (3.3 ml) in dry dichloromethane (10 ml) and heated under reflux for 2.5 hours. The product was evaporated in vacuo to produce an oil which was crystallised from dry tetrahydrofuran to give colourless crystals of 3-piperidinomethylbenzyl chloride hydrochloride (m.p. 156°–160° C.).

A mixture of the above prepared benzyl chloride hydrochloride (1.73 g) and thiourea (0.5 g) in absolute ethanol (14 ml) was boiled under reflux for 16 hours. The reaction mixture was cooled and crystallisation induced to give 2-(3-piperidinomethylbenzyl)isothiourea dihydrochloride as a cream solid (m.p. 224°–226° C.).

A stirred solution of the above isothiourea (1.2 g) and 3-chloropropionitrile (0.4 ml) in a mixture of water (7 ml) and ethanol (5 ml) was treated at 0°–5° C. with 2.5N sodium hydroxide (5.3 ml). The reaction mixture was stirred at 0°–5° C. for a further hour and then allowed to warm to 20° C. The reaction mixture was extracted with ethyl acetate and the extracts washed with water, dried and evaporated to provide 3-(3-piperidinomethylbenzylthio)propionitrile as an oil.

EXAMPLE 41

A stirred suspension of 3-piperidinomethylthiophenol (0.36 g) in dry dimethylformamide (4 ml) was treated with anhydrous potassium carbonate (0.5 g) and stirred for 30 minutes. 4-Bromobutyronitrile (0.18 ml) was then added to the reaction mixture with dimethylformamide (1 ml) and the resultant suspension stirred at room temperature for 48 hours. The resulting product was poured into 5 volumes of water and extracted with ethyl acetate; the extracts were washed with water, dried and evaporated to give 4-(3-piperidinomethylphenylthio)butyronitrile as an orange-red oil.

EXAMPLE 42

In a similar manner to that described above in Example 17 ethyl 4-(3-piperidinomethylphenoxy)butyrate (b.p. 190°–200° C./0.005 mm Hg) was prepared from N-3-hydroxybenzylpiperidine and ethyl 4-bromobutyrate. The resulting ester (21.4 g) was then hydrolysed by heating under reflux with potassium hydroxide (3.6 g), water (210 ml) and industrial methylated spirit (210 ml) for 30 minutes. 5N Hydrochloric acid (13.7 ml) was then added and the solvent removed by evaporation in vacuo. The residue was dried by azeotropic distillation with toluene and then with ethanol. The residue was digested with ethanol (420 ml). The ethanolic liquor was filtered and the solvent removed from the filtrate to give a yellow oil which was crystallised from a mixture of methanol and ether to give 4-(3-piperidinomethylphenoxy)butyric acid (m.p. 73°–77° C.).

EXAMPLE 43

An ice-cold solution of 4-(3-piperidinomethylphenoxy)butyronitrile (0.9 g) prepared as described in Example 17 in a mixture of ethanol (5 ml) and dioxan (5 ml) was saturated with hydrogen chloride gas. The mixture was left for 16 hours during which time the temperature rose to ambient. The solvent was then removed by evaporation to yield a hydrochloride salt of ethyl 4-(3-piperidinomethylphenoxy)butyrimidate as a colourless oil. The imidate salt was mixed with 4-methylcarbamoylmethyl-o-phenylenediamine (0.6 g) prepared as described in Example 8 and ethanol (38 ml) and the mixture was heated under reflux for 4½ hours. The solvent was removed by evaporation in vacuo and the residue dissolved in water. The aqueous solution was washed with ethyl acetate and then aqueous ammonia solution (S.G. 0.880) was added until the solution was alkaline. The solution was extracted with ethyl acetate and the extracts were washed and dried. Partial removal of the ethyl acetate caused crystallisation of 5-methylcarbamoylmethyl-2-[3-(3-piperidinomethylphenoxy)propyl]benzimidazole (m.p. 111°–115° C.) as colourless crystals. [Formula I E=—$(CH_2)_3$.O, J is hydrogen, $R_1$=methyl, $R_2$=H, $NR_3R_4$=piperidino, m=1, and p=1].

In a similar manner to that described in Example 43 compounds of formula I listed in Table IV were obtained. Column A gives the Examples in which the preparation of the diamines of formula II used can be found and column B give the Examples in which the preparation of the cyano compounds of formula III (Z=CN) used can be found.

TABLE IV

| Ex. | A | B | $NR_1R_2$ | $NR_3R_4$ | E | J | m | p | m.p. |
|---|---|---|---|---|---|---|---|---|---|
| 44 | 8 | 18 | methylamino | pyrrolidin-1-yl | $(CH_2)_3$.O | H | 1 | 1 | 132–134° C. |
| 45 | 8 | 31 | methylamino | cyclopropylamino | $(CH_2)_3$.O | H | 1 | 1 | 121–124° C. |
| 46 | 8 | 34 | methylamino | piperidino | $(CH_2)_5$.O | H | 1 | 1 | 97–101° C. |
| 47 | 8 | 25 | methylamino | dimethylamino | $(CH_2)_3$.O | H | 1 | 1 | 116–119° C. |
| 48 | 8 | 40 | methylamino | piperidino | $(CH_2)_2$.S.$CH_2$ | H | 1 | 1 | 144–146° C. |

EXAMPLE 49

In a similar manner to that described in Example 43 2-[3-(3-pyrrolidin-1-ylmethylphenoxy)propyl]-5-pyrrolidin-1-ylcarbonylmethylbenzimidazole was prepared from the product of Example 18 and the diamine prepared as described in Example 1. A solution of the base (0.0032 mole) in ethyl acetate (33 ml) was added to a filtered solution of L(+)-tartaric acid hydrate (0.54 g) in ethyl acetate (215 ml). A precipitate was formed which was separated by filtration and washed with ethyl acetate and petroleum ether (b.p. 40°–60° C.) to give 2-[3-(3-pyrrolidin-1-ylmethylphenoxy)propyl]-5-pyrrolidin-1-ylcarbonylmethylbenzimidazole L(+)-sesquitartrate (m.p. 88°–92° C.). This product was shown by analysis to contain 1 mole of ethyl acetate. [Formula I E=$(CH_2)_3$.O, J=hydrogen, $NR_1R_2$=pyrrolidin-1-yl, $NR_3R_4$=pyrrolidin-1-yl, m=1 and p=1].

EXAMPLES 50 TO 80

In a similar manner to that described in Example 49 the tartrate salts of formula XIV

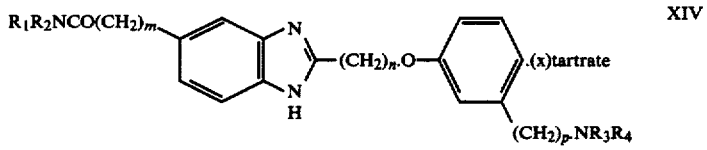

XIV listed in Table V were obtained. Column A gives the Examples in which the preparation of the diamines of formula II used can be found and Column B gives the Examples in which the preparation of the cyano compounds of formula III (Z=CN) used can be found. Many of the salts were obtained as solvates and in Table V, Column y gives the number of moles of ethyl acetate present by analysis and Column z gives the number of moles of water present. Variations from the manner described in Example 49 are identified by the following Notes.

(1) Salt recrystallised from 2-propanol. Product contains 0.25 mole 2-propanol.

(2) Salt recrystallised from 2-propanol. Product contains one mole 2-propanol.

(5) Collapsed at 63° C. then melted at 159° C. with decomposition.

(6) Melted 62°–67° C. then resolidified and melted at 131°–136° C. with decomposition.

(7) Collapsed 58.5° C. then melts at 76°–80° C. Effervescence at 165° C.

(8) Softened and shrank at temperatures above 75° C.

(9) Softened and shrank at 68° C. then gradually decomposes.

(10) Softened and shrank at 73° C. then gradually decomposes.

(11) Softened and shrank at 75° C. then gradually decomposes.

(13) Collapsed at 78°–83° C. then melted at 145° C. with decomposition.

TABLE V

| Ex. | A | B | NR$_1$R$_2$ | NR$_3$R$_4$ | m | n | p | x | y | z | m.p. |
|---|---|---|---|---|---|---|---|---|---|---|---|
| 50 | 1 | 17 | pyrrolidin-1-yl | piperidino | 1 | 3 | 1 | 2 | 2 | | |
| 51 | 1 | 25 | pyrrolidin-1-yl | dimethylamino | 1 | 3 | 1 | 1.7 | 1 | | |
| 52 | 1 | 19 | pyrrolidin-1-yl | hexamethylene-imino | 1 | 3 | 1 | 2 | 1 | | |
| 53 | 1 | 29 | pyrrolidin-1-yl | cyclohexylamino | 1 | 3 | 1 | 1.25 | | 0.5 | 120°(dec) |
| 54 | 1 | 20 | pyrrolidin-1-yl | 4-methyl-piperidino | 1 | 3 | 1 | 1.9 | | 0.3 | 80°(dec) |
| 55 | 1 | 22 | pyrrolidin-1-yl | morpholino | 1 | 3 | 1 | 2.5 | 1 | 1 | 156–160° C. |
| 56 | 1 | 23 | pyrrolidin-1-yl | 2-methyl-pyrrolidin-1-yl | 1 | 3 | 1 | 1.8 | 1 | 0.5 | 106–111° C. |
| 57 | 1 | 39 | pyrrolidin-1-yl | dimethylamino | 1 | 3 | 0 | 1.3 | | 0.2 | |
| 58 | 1 | 24 | pyrrolidin-1-yl | methylamino | 1 | 3 | 1 | 1.9 | 0.7 | 0.75 | 130° C. |
| 59 | 1 | 38 | pyrrolidin-1-yl | pyrrolidin-1-yl | 1 | 3 | 2 | 1.3 | | 0.4 | 85–88° C. |
| 60 | 1 | 28 | pyrrolidin-1-yl | propylamino | 1 | 3 | 1 | 1.3 | 0.05 | | 67–71° C. |
| 61 | 1 | 21 | pyrrolidin-1-yl | 1,2,5,6-tetra-hydropyrid-1-yl | 1 | 3 | 1 | 1.8 | | 1 | 70–72° C. |
| 62 | 2 | 18 | piperidino | pyrrolidin-1-yl | 1 | 3 | 1 | 1 | 0.5 | 0.5 | 79–85° C. |
| 63 | 9 | 18 | methylamino | pyrrolidin-1-yl | 1 | 3 | 1 | 1.25 | 0.5 | 0.5 | |
| 64 | 14 | 17 | dimethylamino | piperidino | 2 | 3 | 1 | 1.8 | 0.1 | 0.7 | |
| 65 | 6 | 17 | pyrrolidin-1-yl | piperidino | 2 | 3 | 1 | 1.75 | 0.1 | 0.9 | |
| 66 | 10 | 17 | dimethylamino | piperidino | 1 | 3 | 1 | 1.5 | 0.5 | 0.6 | |
| 67 | 4 | 18 | 2-methyl-pyrrolidin-1-yl | pyrrolidin-1-yl | 1 | 3 | 1 | 1.75 | | 1 | 93–96° C. |
| 68 | 3 | 25 | 4-methyl-piperazin-1-yl | dimethylamino | 1 | 3 | 1 | 2.2 | 0.5 | 1 | 149–154° C. |
| 69 | 10 | 26 | dimethylamino | diethylamino | 1 | 3 | 1 | 2.2 | 1 | 0.5 | 113–118° C. |
| 70 | 13 | 25 | isopropylamino | dimethylamino | 1 | 3 | 1 | 2.2 | 0.5 | | 49–54°(dec) |
| 71 | 11 | 25 | ethylmethylamino | dimethylamino | 1 | 3 | 1 | 2.55 | 0.1 | 0.6 | 49–54°(dec) |
| 72 | 10 | 25 | dimethylamino | dimethylamino | 1 | 3 | 1 | 2 | | 0.5 | 68–70° C.(dec) |
| 73 | 5 | 25 | morpholino | dimethylamino | 1 | 3 | 1 | 2 | | 0.8 | 60–65° C.(dec) |
| 74 | 10 | 27 | dimethylamino | ethylmethylamino | 1 | 3 | 1 | 1.7 | 0.5 | 0.5 | 130° C.(dec) |
| 75 | 12 | 25 | diethylamino | dimethylamino | 1 | 3 | 1 | 1.5 | 0.2 | 1.3 | 65° C.(dec) |
| 76 | 1 | 33 | pyrrolidin-1-yl | piperidino | 1 | 4 | 1 | 2 | 2 | | 144–149° C. |
| 77 | 15 | 17 | amino | piperidino | 1 | 3 | 1 | 1.75 | 0.75 | | 70°(dec) |
| 78 | 8 | 30 | methylamino | 4-hydroxy-piperidino | 1 | 3 | 1 | 2.6 | 0.6 | 1 | 75°(dec) |
| 79 | 8 | 32 | methylamino | 3-hydroxy-piperidino | 1 | 3 | 1 | 2 | | | |
| 80 | 7 | 17 | azetidin-1-yl | piperidino | 1 | 3 | 1 | 2.1 | | 0.7 | 58.5–60° C. |

(3) Salt recrystallised from 2-propanol. Product contains 0.5 mole 2-propanol.

(12) Salt recrystallised from a mixture of industrial methylated spirit and ethyl acetate. Product contains 0.25 moles ethanol.

The following Notes also apply to Table V and relate to the observed melting point of the products.

(4) Collapsed at 58° C. then melted at 150° C. with decomposition.

EXAMPLE 81

In a similar manner to that described in Example 49, 5-methylcarbamoylmethyl-2-[3-(3-piperidinomethyl-phenylthio)propyl]benzimidazole (1.6)L(+)tartrate [(m.p. 84° C. (dec)] was prepared from the product of Example 41 and the diamine prepared as described in Example 8. The product contained 1 mole of ethyl acetate and 1 mole of water.

EXAMPLE 82

In a similar manner to that described in Example 49, 5-methylcarbamoylmethyl-2-[3-(4-nitro-3-piperidinomethylphenoxy)propyl]benzimidazole L(+)-tartrate [m.p. collapsed at 70°–75° then melted at 130° C. (dec)] was prepared from the product of Example 35 and the diamine prepared as described in Example 8.

EXAMPLE 83

In a similar manner to that described in Example 49, 2-[3-(4-chloro-3-piperidinomethylphenoxy)propyl]-5-methylcarbamoylmethylbenzimidazole L(+)-sesquitartrate [m.p. shrank at 74° then melted at 116° (dec)] was prepared from the product of Example 36 and the diamine prepared as described in Example 8.

EXAMPLE 84

In a similar manner to that described in Example 49 2-[3-(2-chloro-3-piperidinomethylphenoxy)propyl]-5-methylcarbamoylmethylbenzimidazole 1.7 L(+)-tartrate (m.p. 78°–83°) was prepared from the product of Example 37 and the diamine prepared as described in Example 8.

EXAMPLE 85

2-[3-(3-Pyrrolidin-1-ylmethylphenoxy)propyl]-5-pyrrolidin-1-ylcarbonylmethylbenzimidazole (0.54 g) prepared as described in Example 49 was dissolved in the minimum volume of ethanol and a solution of citric acid monohydrate (0.25 g) in ethanol added. The solution was filtered and the volume of the filtrate reduced by evaporation. Addition of acetone gave 2-[3-(3-pyrrolidin-1-ylmethylphenoxy)propyl]-5-pyrrolidin-1-ylcarbonylmethylbenzimidazole (1.9) citrate (m.p. 68° C.). [Formula I E=(CH$_2$)$_3$.O, J=hydrogen, NR$_1$R$_2$=pyrrolidin-1-yl; NR$_3$R$_4$=pyrrolidin-1-yl; m=1 and p=1] The product contained 0.5 mole of acetone.

EXAMPLE 86

The product of Example 49 (5 g) was dissolved in water and the solution basified with aqueous ammonia solution (S.G. 0.880). The resulting solution was extracted with ethyl acetate and the extracts were washed with water and dried. On removal of the solvent by evaporation a brown oil resulted which crystallised on standing. Trituration and ether gave 2-[3-(3-pyrrolidin-1-ylmethylphenoxy)propyl]-5-pyrroldin-1-ylcarbonylmethylbenzimidazole (m.p. 136°–138° C.). [Formula I E=(CH$_2$)$_3$.O, J=hydrogen, NR$_1$R$_2$=pyrrolidin-1-yl; NR$_3$R$_4$=pyrrolidin-1-yl; m=1 and p=1].

EXAMPLE 87

A mixture of ethyl 3,4-diaminobenzoate (0.9 g), 4-(3-piperidinomethylphenoxy)butyric acid (2.1 g) prepared as described in Example 42 and 4N hydrochloric acid (6 ml) was heated and stirred under reflux for 90 minutes. A further portion of the butyric acid (2.1 g) and of 4N hydrochloric acid (6 ml) was added and the mixture heated under reflux for 90 minutes. The reaction mixture was cooled and poured into water (10 volumes). Aqueous ammonia (S.G. 0.880) was added until the solution was alkaline and the mixture was extracted with ethyl acetate. The extracts were washed with water, dried and on removal of the solvent gave a residue which was purified by preparative layer chromatography on silica gel plates using a 1:1 mixture of dichloromethane and methanol to give 5-ethoxycarbonyl-2-[3-(3-piperidinomethylphenoxy)propyl]benzimidazole as an oil.

A solution of the ester prepared as described above (0.8 g) in industrial methylated spirit (15 ml) and 5N sodium hydroxide solution (1 ml) was heated under reflux for seven hours. The reaction mixture was cooled, diluted with water (10 volumes) and neutralised by the addition of glacial acetic acid. The aqueous solution was washed with ethyl acetate and the water removed by evaporation in vacuo to give a product containing 5-carboxy-2-[3-(3-piperidinomethylphenoxy)propyl]benzimidazole which was used without further purification.

Thionyl chloride (0.5 ml) and then two drops of dimethyl formamide were added to a stirred suspension of the acid (0.91 g) prepared as described above in dichloromethane (50 ml). After the mixture had been stirred for one hour at ambient temperature a further portion of thionyl chloride (1 ml) was added and stirring was continued for 24 hours at ambient temperature. The solvent and excess reagent were removed by evaporation and a 33% (w/v) solution (50 ml) of dimethylamine in ethanol added to the residue. The resultant solution was kept at ambient temperature for 16 hours. Removal of the solvent by evaporation gave a residue which was dissolved in water. On adding aqueous ammonia solution (S.G. 0.880) until the solution was alkaline an oil separated which was extracted into ethyl acetate. The ethyl acetate solution was washed with water, dried and the solvent was removed to yield a froth which was dissolved in a further portion of ethyl acetate. The resulting solution was added to a solution of L(+)-tartaric acid hydrate (0.171 g) in ethyl acetate (68 ml) to yield 5-dimethylcarbamoyl-2-[3-(3-piperidinomethylphenoxy)propyl]benzimidazole (1.6)L(+)tartrate which collapsed at 63°–66° C. and decomposed with effervescence at temperatures above 116° C. [Formula I E=—(CH$_2$)$_3$.O, J=hydrogen, R$_1$ and R$_2$=Me; NR$_3$R$_4$=piperidino; m=0 and p=1].

EXAMPLES 88 TO 95

The salts of the product of Example 43 listed below in Table VI have been prepared by treating a solution of the product of Example 43 in ethyl acetate with the appropriate acid. In Table VI the number of moles of ethyl acetate present in the product is given in Column x and the number of moles of water in Column y.

TABLE VI

| Ex. | Salt | x | y | m.p. |
|---|---|---|---|---|
| 88 | (1.4)L(+)tartrate | | 0.25 | shrank 74° melted above 140° C. (dec) |
| 89 | (1.3)hydrochloride | 0.25 | 0.5 | 86–90° (dec) |
| 90 | dinitrate | 0.5 | 0.5 | hydroscopic solid mp. not determined |
| 91 | (1.5)succinate | 0.5 | 0.9 | softens 45° melts at 75° (dec) |
| 92 | citrate | | 1.0 | softens 78° melts at 115° |
| 93 | (1.5)fumarate | | 0.6 | softens 65° melts at 100° |
| 94 | (0.9)oxalate | | 0.75 | shrank 68° melts at 95° |
| 95 | di-p-toluoyltartrate | | 0.5 | 116–120° |

The therapeutic activity of the compounds of Examples 43 to 87 was demonstrated in the following tests:

(1) Histamine H$_2$-receptor antagonist activity was determined by continuously recording spontaneous contraction frequency of an isolated guinea-pig atrial preparation, mounted in a 15 ml organ bath containing Tyrode's solution at 34° C. and bubbled with 95% oxygen and 5% carbon dioxide. Increasing amounts of histamine (from 0.25 to 128 μM) were added sequentially to the organ bath, successive quantities being introduced when a constant response to the preceeding concentration had been reached. Using a digital logic system [Parry, M. and Wood, R. G. (1978) Brit. J. Phramacol., 64, 474P] the constant atrial contraction rate, at each concentration of histamine in the organ bath was measured. The maximal rate at which the heart could be stimulated over the spontaneous rate, by histamine in the absence of the compound under test, was expressed as 100%. The liquid surrounding the atrial preparation was then replaced and the preparation left until the initial contraction frequency was restored. The test compound was added to the organ bath and, after at least a 5 minute wait, a further response curve to histamine was obtained to provide the maximal rate in the presence of the test compound. Each concentration of drug was tested on at least two separate preparations. It is considered that compounds causing a reduction in maximal rate at a concentration in the organ bath of 10 μM or less demonstrate histamine $H_2$-receptor antagonist activity. The compounds of formula I described in Examples 43 to 87 all gave a reduction in the maximal rate when the concentration of test compound in the organ bath was 1 μM or less.

(2) The effect on gastric acid secretion of compounds of formula I was determined in vagally denervated gastric pouch dogs. After an overnight fast, histamine diphosphate was infused intravenously at a rate of 3 $\mu g.kg^{-1}.min.^{-1}$ to produce in each dog a sub-maximal stimulation of gastric acid secretion. Samples of gastric juice were collected at 15 min. intervals. The volumes were measured and the acid concentration determined by titration. When the output of gastric acid was constant as determined by measuring over three consecutive 15 minute periods, the compound of formula I under examination was adminstered orally. Collection of gastric juice was continued at 15 minute intervals for a further 4 hours. Each compound was examined at up to three dose levels in two to four dogs. The maximum fall in acid output over a 15 min. period was determined at each dose-level and the compound was considered active in this test if the secretion of gastirc acid was inhibited at an oral dose of 10 mg/kg or less.

We claim:

1. A compound of the formula I

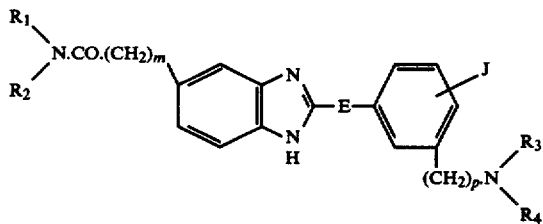

or a pharmaceutically acceptable acid addition salt thereof in which $R_1$ and $R_2$, which are the same or different, and each is hydrogen, alkyl of up to 3 carbon atoms or $R_1$ and $R_2$ together with the nitrogen to which they are attached form a pyrrolidinyl, piperidino, hexamethyleneimino, tetrahydropyridyl, piperazinyl, morpholino, thiomorpholino, methylpyrrolidinyl, methylpiperazinyl, methylpiperidino or azetidinyl ring; $R_3$ is hydrogen, alkyl of 1 to 3 carbon atoms or cycloalkyl of 3 to 6 carbon atoms and $R_4$ is alkyl of 1 to 3 carbon atoms or cycloalkyl of 3 to 6 carbon atoms, or $R_3$ and $R_4$ together with the nitrogen to which they are attached form a pyrrolidinyl, piperidino, hexamethyleneimino, tetrahydropyridyl, piperazinyl, morpholino, thiomorpholino, methylpyrrolidinyl, methylpiperazinyl, methylpiperidino or hydroxypiperidino ring; E is —$(CH_2)_2$—S—$CH_2$—, —$(CH_2)_3$—S— or —$(CH_2)_n$—O—, in which n is 3, 4 or 5; J is hydrogen, halo or nitro; m is 0, 1 or 2; p is 0, 1 or 2.

2. A compound according to claim 1 in which J is chloro.

3. A compound according to claim 1 wherein E is $(CH_2)_nO$, wherein n is 3 or 4 and J is hydrogen.

4. A compound according to claim 1 in which $NR_1R_2$ is amino, methylamino, dimethylamino, isopropylamino, ethylmethylamino, diethylamino, pyrrolidinyl, piperidino, morpholino, methylpyrrolidinyl, methylpiperazinyl or azetidinyl.

5. A compound according to claim 1 in which $NR_1R_2$ is amino, methylamino, dimethylamino, piperidino or pyrrolidinyl.

6. A compound according to claim 1 in which $NR_3R_4$ is methylamino, dimethylamino, diethylamino, ethylmethylamino, propylamino, pyrrolidinyl, piperidino, hexamethyleneimino, tetrahydropyridyl, morpholino, methylpyrrolidinyl, methylpiperidino, hydroxypiperidino, cyclohexylamino or cyclopropylamino.

7. A compound accordingly to claim 1 in which $NR_3R_4$ is dimethylamino, propylamino, piperidino or pyrrolidinyl.

8. 5-methylcarbamoylmethyl-2-benzimidazole or a pharmaceutically acceptable acid addition salt thereof.

9. A pharmaceutical composition useful for treating gastric acid secretion in humans which comprises a therapeutically effective amount of a compound of the formula I:

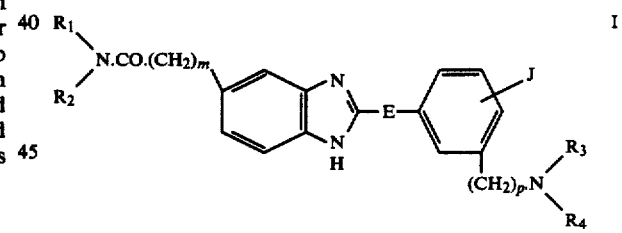

or a pharmaceutically acceptable acid addition salt thereof or a pharmaceutically acceptable acid addition salt thereof in which $R_1$ and $R_2$, which are the same or different, and each is hydrogen, alkyl of up to 3 carbon atoms or $R_1$ and $R_2$ together with the nitrogen to which they are attached form a pyrrolidinyl piperidino, hexamethyleneimino, tetrahydropyridyl, piperazinyl, morpholino, thiomorpholino, methylpyrrolidinyl, methylpiperazinyl, methylpiperidino or azetidinyl ring; $R_3$ is hydrogen, alkyl of 1 to 3 carbon atoms or cycloalkyl of 3 to 6 carbon atoms and $R_4$ is alkyl of 1 to 3 carbon atoms or cycloalkyl of 3 to 6 carbon atoms, or $R_3$ and $R_4$ together with the nitrogen to which they are attached form a pyrrolidinyl, piperidino, hexamethyleneimino, tetrahydropyridyl, piperazinyl, morpholino, thiomorpholino, methylpyrrolidinyl, methylpiperazinyl, methylpiperidino or hydroxypiperidino ring; E is —$(CH_2)_2$—S—$CH_2$—, —$(CH_2)_3$—S— or —$(CH_2)_n$—O—, in which n is 3, 4 or 5; J is hydrogen, halo or nitro; m is 0, 1 or 2; p is 0, 1 or 2 in combination with a pharmaceutically acceptable carrier.

10. A pharmaceutical composition according to claim 9 in which J is chloro.

11. A pharmacuetical composition according to claim 9 wherein E is (CH₂)ₙO, wherein n is 3 or 4 and J is hydrogen.

12. A pharmaceutical composition according to claim 9 in which NR₁R₂ is amino, methylamino, dimethylamino, isopropylamino, ethylmethylamino, diethylamino, pyrrolidinyl, piperidino, morpholino, methylpyrrolidinyl, methylpiperazinyl or azetidinyl.

13. A pharmaceutical composition according to claim 9 in which NR₁R₂ is amino, methylamino, dimethylamino, piperidino or pyrrolidinyl.

14. A pharmaceutical composition according to claim 9 in which NR₃R₄ is methylamino, dimethylamino, diethylamino, ethylmethylamino, propylamino, pyrrolidinyl, piperidino, hexamethyleneimino, tetrahydropyridyl, morpholino, methylpyrrolidinyl, methylpiperidino, hydroxypiperidino, cyclohexylamino or cyclopropylamino.

15. A pharmaceutical composition accordingly to claim 9 in which NR₃R₄ is dimethylamino, propylamino, piperidino or pyrrolidinyl.

16. A pharmaceutical composition according to claim 9 wherein the compound is 5-methylcarbamoylmethyl-2-[3-(3-piperidinomethylphenoxy)propyl]benzimidazole or a pharmaceutically acceptable acid addition salt thereof.

17. A method of treating peptic ulceration or other diseases caused by or exacerbated by gastric acid in humans which comprises administering to a human in need thereof a therapeutically effective amount of a compound of the formula I:

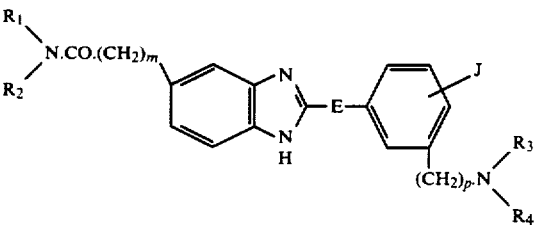

or a pharmaceutically acceptable acid addition salt thereof in which R₁ and R₂, which are the same or different, and each is hydrogen, alkyl of up to 3 carbon atoms or R₁ and R₂ together with the nitrogen to which they are attached form a pyrrolidinyl piperidino, hexamethyleneimino, tetrahydropyridyl, piperazinyl, morpholino, thiomorpholino, methylpyrrolidinyl, methylpiperazinyl, methylpiperidino or azetidinyl ring; R₃ is hydrogen, alkyl of 1 to 3 carbon atoms or cycloalkyl of 3 to 6 carbon atoms and R₄ is alkyl of 1 to 3 carbon atoms or cycloalkyl of 3 to 6 carbon atoms, or R₃ and R₄ together with the nitrogen to which they are attached form a pyrrolidinyl, piperidino, hexamethyleneimino, tetrahydropyridyl, piperazinyl, morpholino, thiomorpholino, methylpyrrolidinyl, methylpiperazinyl, methylpiperidino or hydroxypiperidino ring; E is —(CH₂)₂—S—CH₂—, —(CH₂)₃—S— or —(CH₂)ₙ—O—, in which n is 3, 4 or 5; J is hydrogen, halo or nitro; m is 0, 1 or 2; p is 0, 1 or 2 in combination with a pharmaceutically acceptable carrier.

18. A method according to claim 17 in which J is chloro.

19. A method according to claim 17 wherein E is (CH₂)ₙO, wherein n is 3 or 4 and J is hydrogen.

20. A method according to claim 17 in which NR₁R₂ is amino, methylamino, dimethylamino, isopropylamino, ethylmethylamino, diethylamino, pyrrolidinyl, piperidino, morpholino, methylpyrrolidinyl, methylpiperazinyl or azetidinyl.

21. A method according to claim 17 in which NR₁R₂ is amino, methylamino, dimethylamino, piperidino or pyrrolidinyl.

22. A method according to claim 17 in which NR₃R₄ is methylamino, dimethylamino, diethylamino, ethylmethylamino, propylamino, pyrrolidinyl, piperidino, hexamethyleneimino, tetrahydropyridyl, morpholino, methylpyrrolidinyl, methylpiperidino, hydroxypiperidino, cyclohexylamino or cyclopropylamino.

23. A method accordingly to claim 17 in which NR₃R₄ is dimethylamino, propylamino, piperidino or pyrrolidinyl.

24. A method according to claim 17 wherein the compound is 5-methylcarbamoylmethyl-2-[3-(3-piperidinomethylphenoxy)propyl]benzimidazole or a pharmaceuticallly acceptable acid addition salt thereof.

25. A method of antagonising histamine H₂-receptors in humans which comprises administering to a human in need thereof a histamine H₂-antagonising amount of a compound of the formula I:

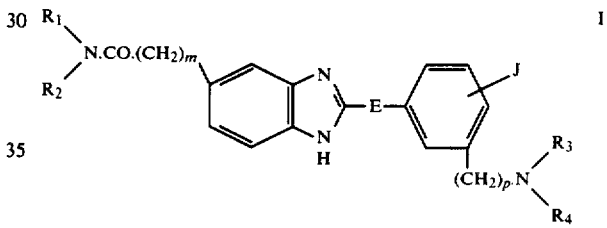

or a pharmaceutically acceptable acid addition salt thereof in which R₁ and R₂, which are the same or different, and each is hydrogen, alkyl of up to 3 carbon atoms or R₁ and R₂ together with the nitrogen to which they are attached form a pyrrolidinyl piperidino, hexamethyleneimino, tetrahydropyridyl, piperazinyl, morpholino, thiomorpholino, methylpyrrolidinyl, methylpirazinyl, methylpiperidino or azetidinyl ring; R₃ is hydrogen, alkyl of 1 to 3 carbon atoms or cycloalkyl of 3 to 6 carbon atoms and R₄ is alkyl of 1 to 3 carbon atoms or cycloalkyl of 3 to 6 carbon atoms, or R₃ and R₄ together with the nitrogen to which they are attached form a pyrrolidinyl, piperidino, hexamethyleneimino, tetrahydropyridyl, piperazinyl, morpholino, thiomorpholino, methylpyrrolidinyl, methylpiperazinyl, methylpiperidino or hydroxypiperidino ring; E is —(CH₂)₂—S—CH₂—, —(CH₂)₃—S— or —(CH₂)ₙ—O—, in which n is 3, 4 or 5; J is hydrogen, halo or nitro; m is 0, 1 or 2; p is 0, 1 or 2 in combination with a pharmaceutically acceptable carrier.

26. A method according to claim 25 in which J is chloro.

27. A method according to claim 25 wherein E is (CH₂)ₙO, wherein n is 3 or 4 and J is hydrogen.

28. A method according to claim 25 in which NR₁R₂ is amino, methylamino, dimethylamino, isopropylamino, ethylmethylamino, diethylamino, pyrrolidinyl, piperidino, morpholino, methylpyrrolidinyl, methylpiperazinyl or azetidinyl.

29. A method according to claim 25 in which $NR_1R_2$ is amino, methylamino, dimethylamino, piperidino or pyrrolidinyl.

30. A method according to claim 25 in which $NR_3R_4$ is methylamino, dimethylamino, diethylamino, ethylmethylamino, propylamino, pyrrolidinyl, piperidino, hexamethyleneimino, tetrahydropyridyl, morpholino, methylpyrrolidinyl, methylpiperidino, hydroxypiperidino, cyclohexylamino or cyploroylamino.

31. A method accordingly to claim 25 in which $NR_3R_4$ is dimethylamino, propylamino, piperidino or pyrrolidinyl.

32. A method according to claim 25 wherein the compound is 5-methylcarbamoylmethyl-2-[3-(3-piperidinomethylphenoxy)propyl]benzimidazole or a pharmaceuticallly acceptable acid addition salt thereof.

* * * * *